(12) United States Patent
LaMotte et al.

(10) Patent No.: US 7,135,987 B1
(45) Date of Patent: Nov. 14, 2006

(54) WIRELESS CHART RECORDER SYSTEM AND METHOD

(75) Inventors: Robert LaMotte, Ashland, MA (US);
William Perry, Sharon, MA (US);
William Saltzstein, Woodinville, WA (US)

(73) Assignee: GSI Group Corporation, Billerica, MA (US)

( * ) Notice: Subject to any disclaimer, the term of this patent is extended or adjusted under 35 U.S.C. 154(b) by 486 days.

(21) Appl. No.: 10/448,570

(22) Filed: May 30, 2003

Related U.S. Application Data

(60) Provisional application No. 60/385,267, filed on Jun. 3, 2002.

(51) Int. Cl.
*G08B 23/00* (2006.01)
(52) U.S. Cl. ............... 340/870.07; 600/300; 128/903; 128/920
(58) Field of Classification Search ........... 340/870.07; 600/300; 128/903, 920
See application file for complete search history.

(56) References Cited

U.S. PATENT DOCUMENTS

| | | | | |
|---|---|---|---|---|
| 3,921,621 A | * | 11/1975 | Baessler | ............ 600/549 |
| 4,253,104 A | | 2/1981 | Paulsen | |
| 4,546,436 A | * | 10/1985 | Schneider et al. | ......... 600/361 |
| 4,862,144 A | * | 8/1989 | Tao | ............ 340/573.1 |
| 5,144,284 A | * | 9/1992 | Hammett | ......... 340/573.1 |
| 5,373,852 A | | 12/1994 | Harrison et al. | |
| 5,381,136 A | | 1/1995 | Powers et al. | |
| 5,474,574 A | * | 12/1995 | Payne et al. | ............ 607/7 |
| 5,499,626 A | * | 3/1996 | Willham et al. | ......... 600/300 |
| 5,685,314 A | | 11/1997 | Geheb et al. | |
| 5,687,717 A | * | 11/1997 | Halpern et al. | ......... 600/300 |
| 5,713,350 A | * | 2/1998 | Yokota et al. | ......... 600/300 |
| 5,865,733 A | | 2/1999 | Malinouskas et al. | |
| 6,238,344 B1 | | 5/2001 | Gamelsky et al. | |
| 6,255,800 B1 | | 7/2001 | Bork | |
| 6,263,503 B1 | | 7/2001 | Margulis | |
| 6,363,282 B1 | | 3/2002 | Nichols et al. | |
| 6,375,614 B1 | * | 4/2002 | Braun et al. | ......... 600/300 |
| 6,385,593 B1 | | 5/2002 | Linberg | |
| 6,386,882 B1 | | 5/2002 | Linberg | |
| 6,389,457 B1 | | 5/2002 | Lazaridis et al. | |
| 6,392,486 B1 | | 5/2002 | Lemay, Jr. | |
| 6,392,546 B1 | | 5/2002 | Smith | |

\* cited by examiner

*Primary Examiner*—Timothy Edwards, Jr.
(74) *Attorney, Agent, or Firm*—Gauthier & Connors LLP

(57) ABSTRACT

A system is disclosed for recording continuous streaming data. The system includes a data collection unit, a wireless data transmission unit, a wireless data reception unit and a recorder unit. The data collection unit is for continuously collecting data at a data collection frequency, $f_C$ and providing collected data. The wireless data transmission unit is for continuously transmitting the collected data at a data transmission frequency, $f_T$ where $f_C$ is greater than $f_T$. The wireless data reception unit is for continuously receiving collected data at a data reception frequency, $f_R$ where $f_R$ is equal to $f_T$. The recorder unit is for providing a recorder output of the collected data at a frequency of $f_O$ where $f_O$ is equal to $f_T$.

10 Claims, 8 Drawing Sheets

WIRELESS CHART RECORDER SYSTEM AND METHOD

PRIORITY DATA

This application claims the benefit of U.S. Provisional Patent Appln. Ser. No. 60/385,267 filed on Jun. 3, 2002.

BACKGROUND OF THE INVENTION

Although wireless devices have become common in a variety of applications, certain applications have yet been unable to fully benefit from wireless technology. For example, certain wireless devices provide on/off switching, such as remote key access and locking devices for automobiles and automated garage door openers. Other wireless devices provide personal communication, such as cellular telephones. Further wireless devices provide for the use of wireless keyboards, monitors and printers in computer systems.

One area that has not yet fully benefited from the use of wireless devices is medical applications within an emergency care providing environment, such as in a hospital emergency room or inside an ambulance. Although wireless devices are used in emergency medical environments, such devices typically involve receivers that are dedicated to receive data from a specific transmitter device. In an emergency medical environment, it is desirable to very quickly begin monitoring a patient for a variety of continuous signals, such as pulse, electrocardiogram signals etc. Equipment for providing such monitoring must be attached to the patient and connected to monitoring equipment. This requires time, which is critical, and may obstruct access to the patient due to the presence of wires leading to the monitoring equipment.

For example, U.S. Pat. No. 5,685,314 discloses a patient monitoring system including an auxiliary docking station that may be connected with a monitor system via a single connector that provides for multiple simultaneous connections. ('314 patent, col. 3, lines 4–14). Although such a system may save time, the presence of the wires may provide an obstruction in some situations.

A wireless optical patient monitoring apparatus is disclosed in U.S. Pat. No. 5,865,733 that includes optical sources that attach to a patient and an optical receiver including photodetectors for receiving fetal monitoring signals from the patient. The optical sensors are disclosed to be hard-wire connected to a fetal monitoring console that includes a chart recorder. The '733 patent discloses that the use of optical transmission is preferred over radio frequency transmission where multiple patients may be monitored in the same hospital ('733 patent, col. 1, lines 46–59).

A medical diagnostic ultrasound imaging system is disclosed in U.S. Pat. No. 6,238,344 that includes wireless communication via infrared signals to a controlled peripheral, and states that the controlled peripheral may be, inter alia, a VCR, a DVD player/recorder, a printer, a multi-image camera, a strip-chart recorder, a computer or a robot. ('344 patent, col. 2, lines 38–43). The '344 patent discloses that individual commands be transmitted via the wireless channel and that the peripheral devices (preferably a VCR) be programmed to respond to the commands in a specific fashion. ('344 patent, col. 3, lines 2–16 and col. 4, lines 9–10).

There is a need for a wireless device that is capable of receiving continuous data in real time. Although certain wireless communication systems exist in certain non-medical applications, such devices have not been suitable for use in transmitting continuous data in real time as required, for example for chart recorders in medical applications.

A remote data collection and monitoring system for a distribution line is disclosed in U.S. Pat. No. 5,381,136 that includes a plurality of remote data collecting units that provides operation data to the central controller via a radio frequency transmission system when prompted by the central controller. Although each data collecting unit may include a chart recorder, the data that is sent via radio frequency transmission to the central controller when requested includes alarm related data only.

U.S. Pat. No. 6,389,457 discloses a wireless data transmission system in which each remote user unit is able to select certain data from a central host system and the selected data is then pushed to the remote user unit. The pushed data is repackaged and sent via electronic mail (email) responsive to the triggering event of the user selecting the data.

There is a need, therefore, for a wireless chart recorder that is able to print continuous streaming data in real time. Three is further a need for a wireless chart recorder that is able to select from a variety of input signals, a particular input signal that is recorded in a continuous fashion.

SUMMARY OF THE INVENTION

In accordance with an embodiment, the invention provides a system for recording continuous streaming data. The system includes a data collection unit, a wireless data transmission unit, a wireless data reception unit and a recorder unit. The data collection unit is for continuously collecting data at a data collection frequency, $f_C$ and providing collected data. The wireless data transmission unit is for continuously transmitting the collected data at a data transmission frequency, $f_T$ where $f_C$ is greater than $f_T$. The wireless data reception unit is for continuously receiving collected data at a data reception frequency, $f_R$ where $f_R$ is equal to $f_T$. The recorder unit is for providing a recorder output of the collected data at a frequency of $f_O$ where $f_O$ is equal to $f_T$.

BRIEF DESCRIPTION OF THE DRAWINGS

The following description may be further understood with reference to the accompanying drawings in which.

The drawings are shown for illustrative purposes and are not to scale.

DETAILED DESCRIPTION OF THE ILLUSTRATED EMBODIMENTS

It has been discovered that continuous streaming data may be transmitted via radio frequency signals in real time to a remote chart recorder in accordance with the invention.

Figure 1:
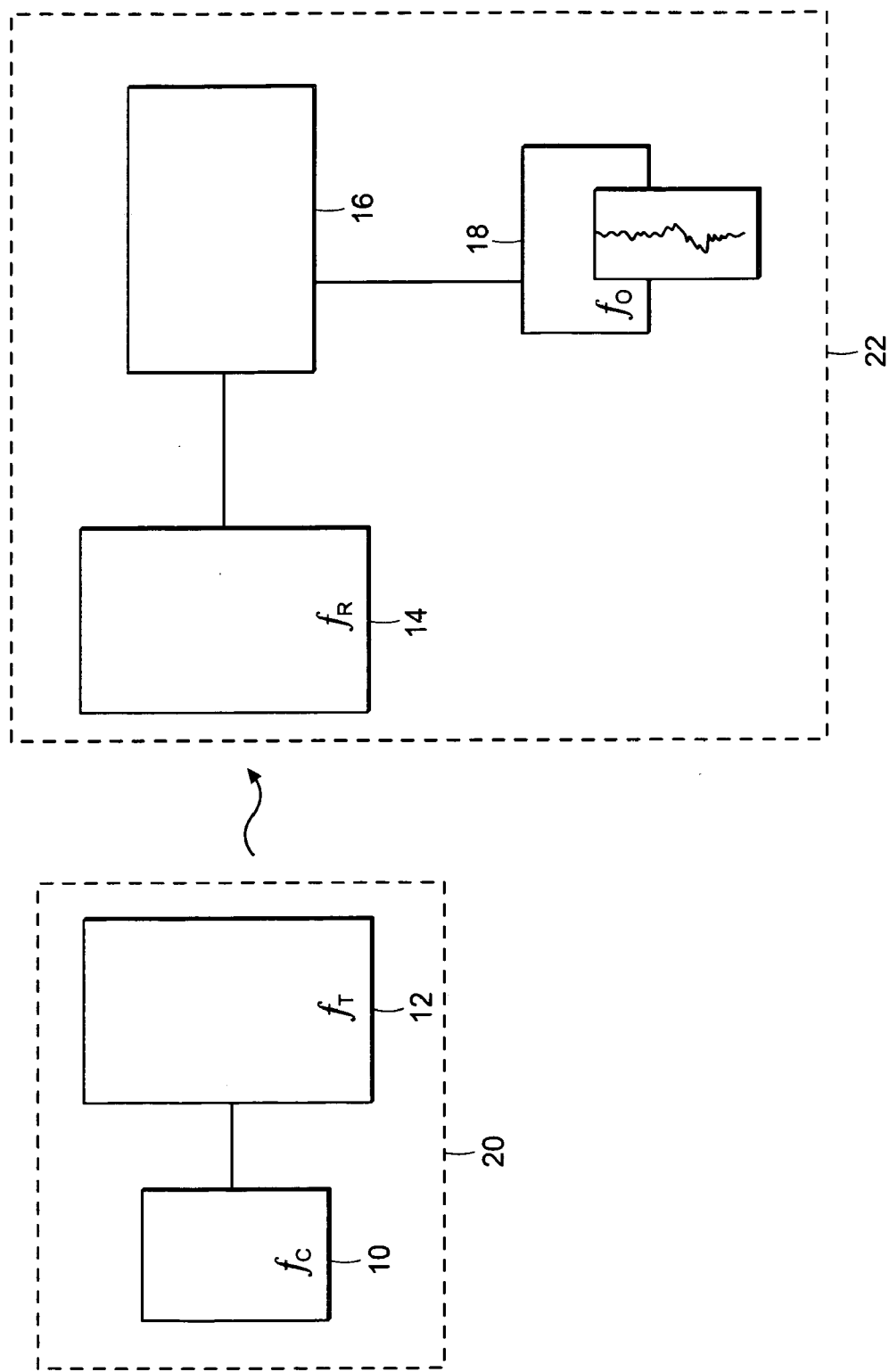
FIG. 1 shows a diagrammatic view of a system in accordance with an embodiment of the invention.

As shown in FIG. 1, a system in accordance with an embodiment of the invention includes a data collection unit 10 such as a heart monitor, a data transmission unit 12, a data reception unit 14, a computer processor controller 16 and a chart recorder 18. The data collection unit 10 provides collected continuous streaming data at a frequency of, for example, 100 samples per second. The data is sent via radio frequency communication (at a frequency of for example, 75 samples per second) to the reception unit 14, which is coupled to the controller 16. The controller 16 receives the streaming data at a data port (e.g., an RS-232 port, an RS-422 port, an RS-485 port etc.) and directs the data in real time to the chart recorder 18. In certain embodiments the data collection unit 14 and data transmission unit may be enclosed within a transmission assembly 20 and the data reception unit 14, controller 16 and recorder 18 may be enclosed within a receiver assembly 22.

The data collected by the collection unit 10 is sampled at a desirable rate suitable for transmission via the radio frequency transmission system. In the present embodiment, the radio frequency transmitter and receiver operate under the Bluetooth wireless standard (Bluetooth is a trademark of Telefonaktiebolaget L.M. Ericsson of Sweeden). In other embodiments the transmitter and receiver may operate under a variety of standards such as the Institute of Electrical and Electronic Engineers (IEEE) 802.11 wireless standard or HomeRF standard etc. (Home RF is a trademark of HomeRF Working Group, Inc. of Portland Oreg.). The transmission frequencies may be, for example, 2.4 GHz or 2.5 GHz and the recorder may display waveforms up to about 500 Hz.

Figure 2:
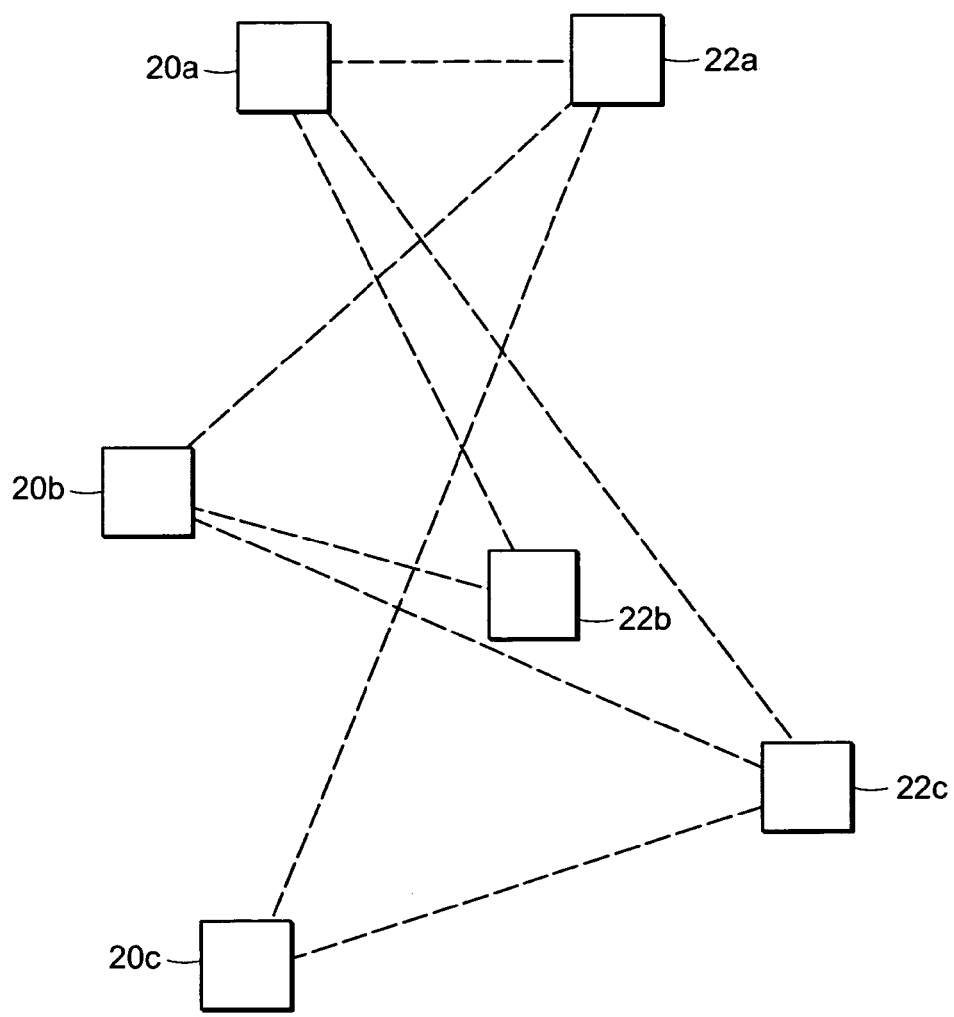
FIG. 2 shows a diagrammatic view of another system in accordance with another embodiment of the invention.

As shown in FIG. 2, in certain embodiments a plurality of data transmission assemblies 20a, 20b and 20c may be employed, and a plurality of data receiver assemblies 22a, 22b and 22c may be employed. The controller 16 in each data receiver assembly may determine which of the plurality of signals that it receives is the strongest signal and may then print the streaming data in real time. The data transmission assemblies may be designed to produce a relatively low power signal that becomes too weak to be detected beyond for example ten feet. For example, as shown in FIG. 2, the data receiver assembly 22a may receive signals from each of the transmission assemblies 20a, 20b and 20c, but would select the signal from transmission assembly 20a because it is closest and therefore the strongest signal. In this way, the receivers and/or transmitters may be moved and automatically begin recording data from the closest transmitter or receiver.

Figure 3A:
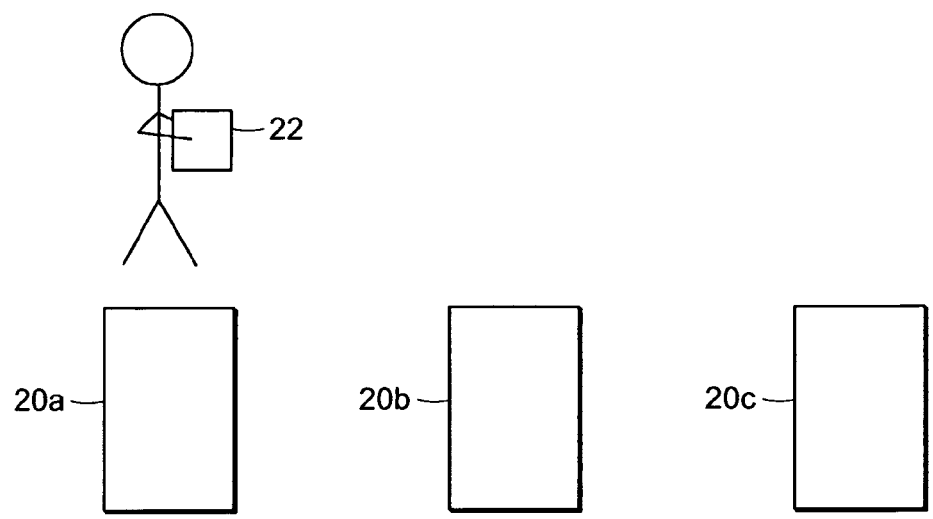
FIGS. 3A and 3B show diagrammatic illustrative views of an implementation of a system in accordance with an embodiment of the invention.
Figure 3B:
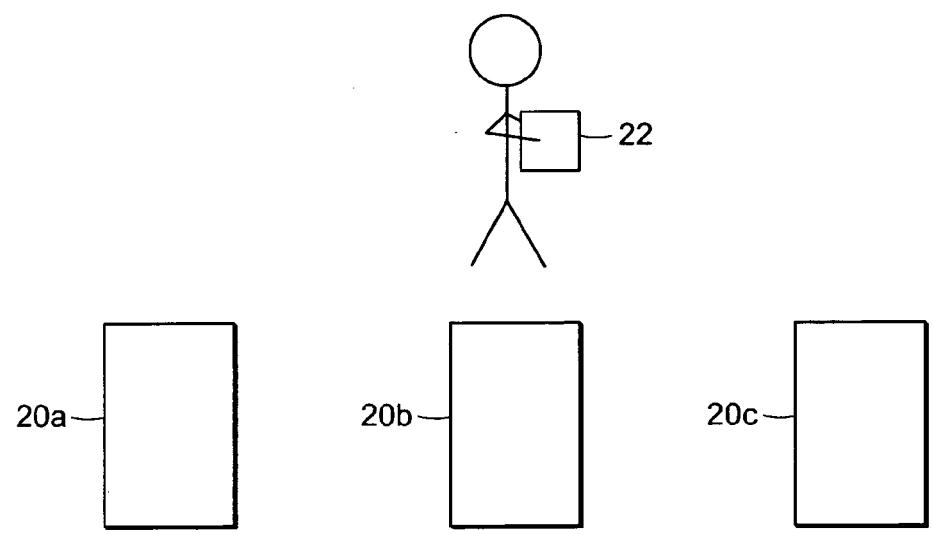

For example, as shown in FIGS. 3 and 3B, a person carrying a receiving assembly 22 may present the assembly 22 to one of a plurality of transmission assemblies 20a–20c. The receiving assembly 22 will record data from transmission assembly 20a when it is closest to assembly 20a (as shown in FIG. 3A) and will record data from transmission assembly 20b when it is closest to assembly 20b (as shown in FIG. 3B). Each receiving unit may, for example, weigh less than 5 lbs.

Figure 4A:
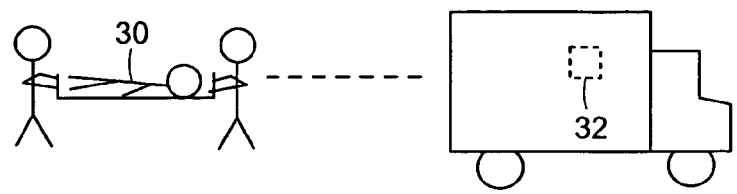
FIGS. 4A and 4B show diagrammatic illustrative views of further implementations of system in accordance with other embodiments of the invention.
Figure 4B:
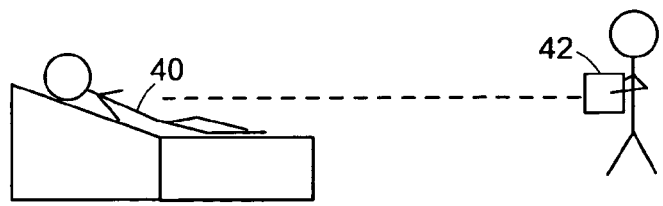

In medical emergency care providing environments, the transmission assembly 30 may be located on a patient and the receiving assembly 32 may be located in an ambulance as shown in FIG. 4A. In this fashion, the recorder may begin printing emergence medical data in real time as the patient is brought into the ambulance without the need to attach wires from the patient to the ambulance equipment. When the patient reaches the hospital, other receiving assemblies in the hospital may pick up the data and print it in the emergency room. In further emergency care providing environments the transmission assembly 40 may be positioned on a patient and the receiving assembly 42 may be temporarily brought into a patient's room to record data without the need to attached cumbersome wires to the patent.

Figure 5:
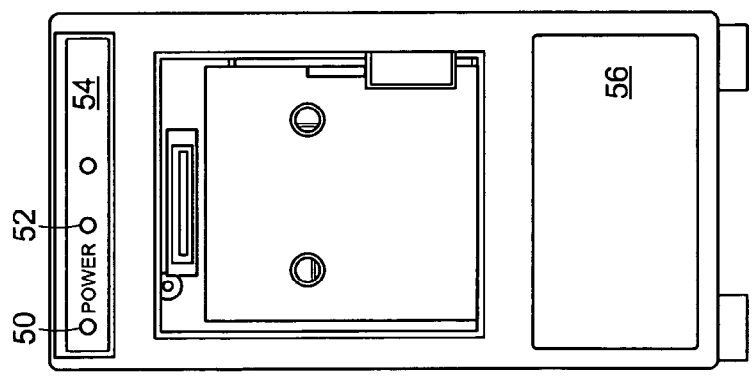
FIG. 5 shows an illustrative front view of a wireless chart recorder assembly in accordance with an embodiment of the invention.

As shown in FIG. 5, the front of a receiving assembly in accordance with an embodiment of the invention includes a panel display 54 including a power indicator 50 and a data detection indicator 52 that is indicative of whether data is being received by the assembly. The chart recorder paper may be produced from the assembly at the output unit 56 as shown. The rear of the receiving assembly of FIG. 5 may include a plurality of access ports 60, 66 and 70, connection ports and hardware 62, 63, 68 and 69, as well as various informative warnings and labels 61, 64 and 67 as shown in FIG. 6.

Figure 6:
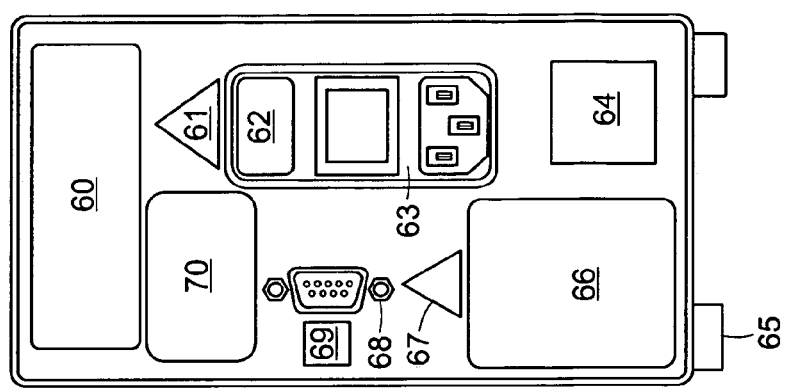
FIG. 6 shows an illustrative rear view of the wireless chart recorder assembly of FIG. 5.
Figure 7:
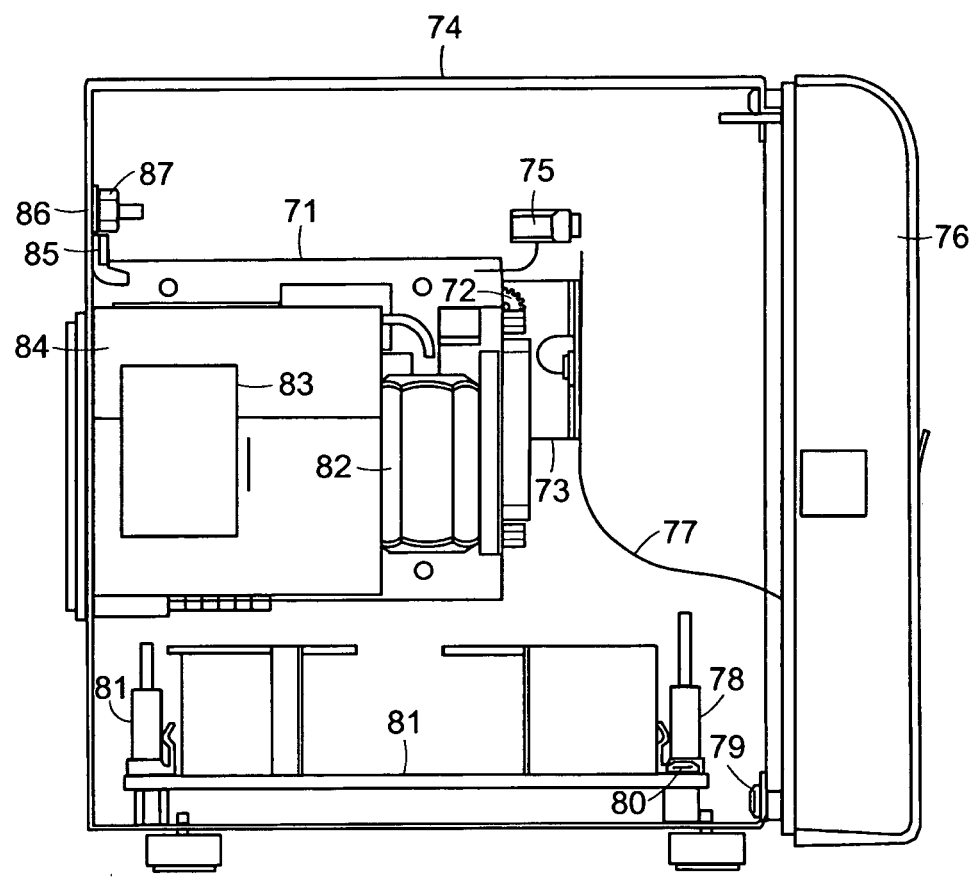
FIG. 7 shows an illustrative side view of the wireless chart recorder assembly of FIG. 5 with the housing removed.
Figure 9:
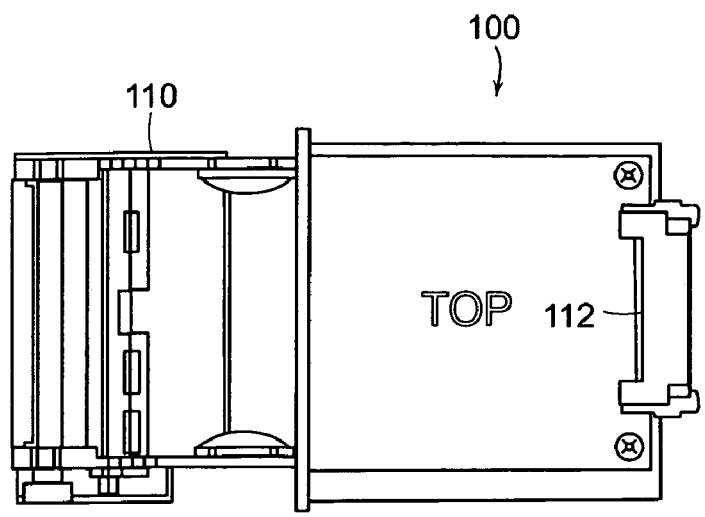
FIG. 9 shows an illustrative top view of the chart recorder of FIG. 8.
Figure 8:
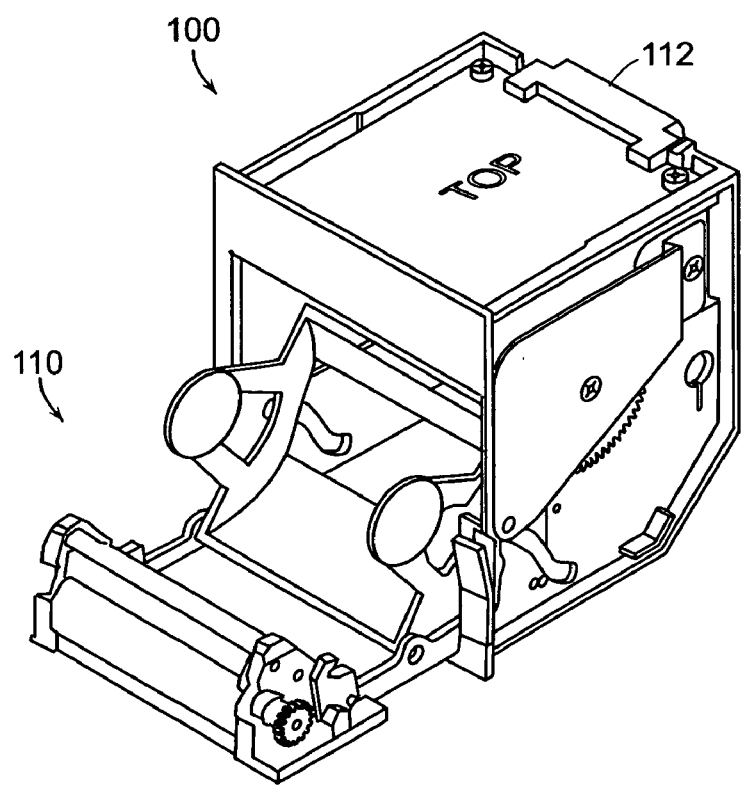
FIG. 8 shows an illustrative isometric view of a chart recorder used in the wireless chart recorder assembly shown in FIGS. 5–7.
Figure 10:
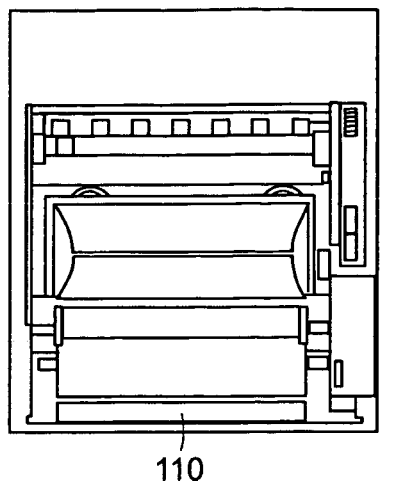
FIG. 10 shows an illustrative front view of the chart recorder of FIG. 8.
Figure 11:
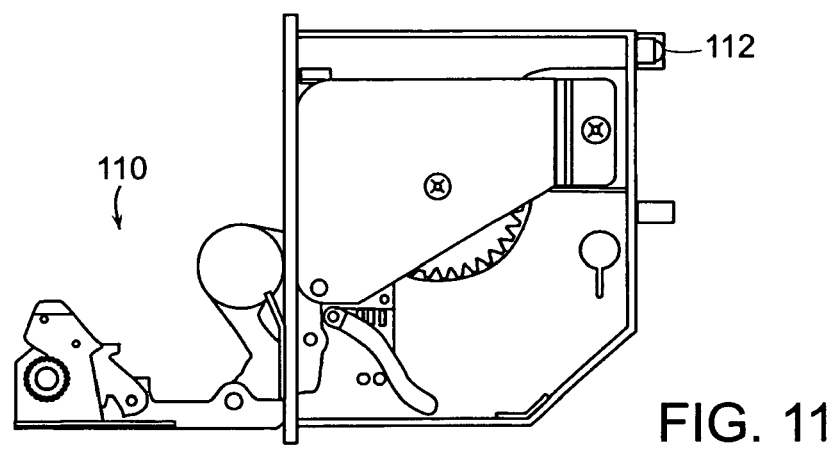
FIG. 11 shows an illustrative side view of the chart recorder of FIG. 8 with the chart recorder housing removed.
Figure 12:
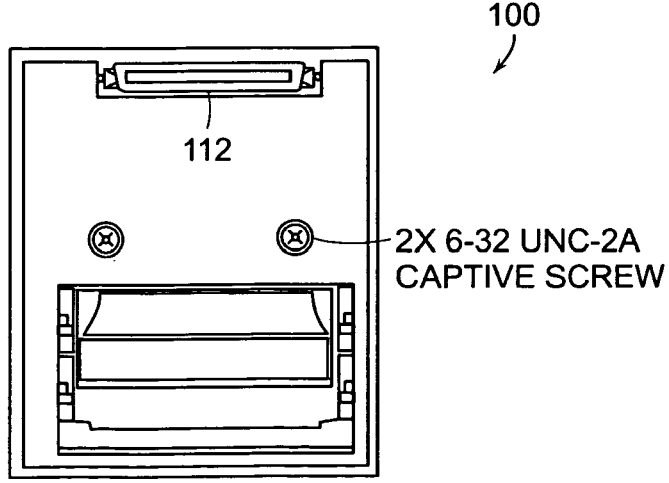
FIG. 12 shows an illustrative rear view of the chart recorder of FIG. 8.

The inside of the receiving assembly shown in FIGS. 5 and 6 is shown in FIG. 7 with the housing removed. The assembly includes a detachable front panel 76 that is coupled to the unit via mounting structure 79, a printer roller cam 77, a printer paper sensor 75, a printer head 73 and a printer advance roller 72. The assembly also includes a controller frame 71 that is connected to the assembly frame via a nut and bolt assembly 86 and 87 that attach a bracket 85 to the assembly frame. The controller frame 71 supports a processor 84, a radio frequency input device 83 and a printer controller 82. The assembly also includes a base assembly 81 and leveling devices 81 and 80.

As shown in FIGS. 8–12, the chart recorder 100 for use with a receiving assembly of the invention may include a cantilevered spring arm mounting assembly 110 that permits a roll of chart recorder paper to be automatically loaded into the chart recorder by closing the mounting assembly 110. When the mounting assembly 110 is shut, rollers on the mounting assembly engage rollers within the chart recorder and automatically capture the chart paper for printing. The chart recorder 100 may be coupled to the receiving assembly processor via an RS-232 port 1112.

Those skilled in the art will appreciate that numerous modifications and variations may be made to the above disclosed embodiments without departing from the spirit and scope of the invention.

What is claimed is:

1. A system for recording continuous streaming data, said system comprising:

data collection means for continuously collecting data at a data collection frequency, $f_C$ and providing collected data, wireless data transmission means for continuously transmitting said collected data at a data transmission frequency, $f_T$ where $f_C$ is greater than $f_T$, wireless data reception means for continuously receiving collected data at a data reception frequency, $f_R$ where $f_R$ is equal to $f_T$, and recorder means for providing a recorder output of said collected data at a frequency of $f_O$ where $f_O$ is equal to $f_T$.

2. The system as claimed in claim 1, wherein said data collection means includes a sensor for collecting data at a frequency of $f_C$=100 Hz.

3. The system as claimed in claim 1, wherein said wireless data transmission means includes a radio frequency transmitter for transmitting data at a frequency of $f_T$=75 Hz.

4. The system as claimed in claim 1, wherein said recorder means includes a chart recorder and a computer processor for providing the recorder output at a frequency of $f_O$=100 Hz.

5. A system for recording continuous streaming data in a medical environment, said system comprising:

medical data collection means for continuously collecting medical data at a data collection frequency, $f_C$ and providing collected medical data, wireless data transmission means for continuously transmitting said collected medical data at a data transmission frequency, $f_T$ where $f_C$ is greater than $f_T$, wireless data reception means for continuously receiving collected medical data at a data reception frequency, $f_R$ where $f_R$ is equal to $f_T$, and chart recorder means for providing a chart recorder output of said collected medical data at a frequency of $f_O$ where $f_O$ is equal to $f_T$.

6. The system as claimed in claim 5, wherein said wireless data transmission means and said wireless data reception means includes Bluetooth compatible components.

7. The system as claimed in claim 5, wherein said medical data collection means further includes a plurality of wireless data reception units for continuously receiving streaming data from a plurality of data transmission units.

8. The system as claimed in claim 5, wherein said system is used in an emergency medical care providing environment.

9. The system as claimed in claim 5, wherein said chart recorder means is located in an ambulance.

10. The wireless chart recorder system as claimed in claim 9, wherein said chart recorder means is readily moveable within a hospital emergency room.

* * * * *

UNITED STATES PATENT AND TRADEMARK OFFICE
CERTIFICATE OF CORRECTION

| | | |
|---|---|---|
| PATENT NO. | : 7,135,987 B1 | Page 1 of 1 |
| APPLICATION NO. | : 10/448570 | |
| DATED | : November 14, 2006 | |
| INVENTOR(S) | : Robert LaMotte et al. | |

It is certified that error appears in the above-identified patent and that said Letters Patent is hereby corrected as shown below:

In Col. 4, line 54, please delete "1112" and replace with --112--.

Signed and Sealed this

Second Day of January, 2007

JON W. DUDAS
*Director of the United States Patent and Trademark Office*